United States Patent [19]
Yoon et al.

[11] Patent Number: 5,725,488
[45] Date of Patent: Mar. 10, 1998

[54] PRINTED FIBERGLASS BANDAGES AS ORTHOPAEDIC CASTING TAPES

[75] Inventors: Hee Kyung Yoon, Easton; Edward L. Cho, Taunton, both of Mass.

[73] Assignee: Johnson & Johnson Professional, Inc., Raynham, Mass.

[21] Appl. No.: 836,032

[22] Filed: Feb. 14, 1992

[51] Int. Cl.⁶ ............................................. A61L 15/00
[52] U.S. Cl. ............................ 602/8; 602/44; 602/41
[58] Field of Search ........................ 602/4, 5, 6, 7, 602/8, 9; 428/255, 273

[56] References Cited

U.S. PATENT DOCUMENTS

| | | | |
|---|---|---|---|
| 4,433,680 | 2/1984 | Yoon | 602/8 |
| 4,627,424 | 12/1986 | Baron | 602/8 |
| 4,934,356 | 6/1990 | Klintworth, Jr. | 602/8 |
| 4,935,019 | 6/1990 | Papp | 602/41 |
| 5,052,380 | 10/1991 | Polta | 602/8 |
| 5,088,484 | 2/1992 | Freeman | 602/8 |
| 5,342,291 | 8/1994 | Scholz et al. | 602/41 |

FOREIGN PATENT DOCUMENTS 0 479 269A1   5/1993   European Pat. Off. .

*Primary Examiner*—Robert A. Hafer
*Assistant Examiner*—Benjamin Koo

[57] ABSTRACT

A printed orthopaedic casting bandage is disclosed having a bandage substrate made of at least 50% fibers having a Young's Modulus in excess of $8 \times 10^6$ psi. The fibers, in particular, are glass fibers and carbon fibers. The printing substance is a plastisol-based printing agent, and the printed substrate is covered with a water-activatable hardening resin such as a polyurethane prepolymer of polyol and isocyanate.

8 Claims, 1 Drawing Sheet

PRINTED FIBERGLASS BANDAGES AS ORTHOPAEDIC CASTING TAPES

This invention relates to the field of orthopaedic bandages and, in particular, resin-coated bandages for use in fracture fixation.

BACKGROUND OF THE INVENTION

U.S. patent application Ser. No. 593,852 entitled, "Orthopaedic Casting Bandage" issuing on Feb. 18, 1992 as U.S. Pat. No. 5,088,484 describes a printed orthopaedic casting bandage. The disclosure of that patent is incorporated herein by reference.

Polymeric casting materials have gained widespread commercial acceptance during the past decade. As compared to plaster of Paris casts, the polymeric or so-called "synthetic" casting materials have advantages of being light weight and strong. Synthetic casting materials are also porous in the hardened state so that the cast is breathable. Typically, orthopaedic synthetic casts are made from a curable resin-impregnated, narrow fabric tape. The fabric, which is preferably knit, can be formed of glass fibers and/or synthetic fibers such as polyester, nylon, polyolefins and the like.

Polyurethane casting materials which have experienced widespread commercial acceptance are disclosed in U.S. Pat. No. 4,433,680 to Yoon. The disclosure of the '680 patent is incorporated herein by reference. These casting materials employ a water-activatable, polyurethane, prepolymer which contains a dimorpholinodiethylether catalyst. The compositions have a long shelf life during which the polyurethane prepolymer remains in the resin state. When the bandage is to be used, it is dipped in water for several seconds and then is removed from the water and applied to the patient usually over a tubular, knitted fabric and a padding. The bandage will set rapidly to a condition where it is capable of immobilizing a fracture.

U.S. Pat. No. 5,088,484 discloses a cast bandage which comprises an open-mesh fibrous tape having a hardenable resin coated on the fibrous tape which is capable of curing to form a hardened plastic. The tape has applied thereto at least one coloring agent which is visibly disposed on at least a portion of the fibrous tape, the coloring agent is stablely retained by the fibrous tape in the presence of hardenable liquid resin.

In attempting to print on cast bandages made from fiberglass substrate, there have been several problems identified. One of them is a poor physical bond between the printing ink and the fiberglass filaments. The nature of the fiberglass surface is not capable of absorbing most dyes or pigments preventing the good adhesion necessary to maintain the pigment in the presence of the curable resin.

Many of the printing inks which can be used to print fiberglass substrates were solvated and bled after the polyurethane resin was applied. Sometimes the printing ink itself provided chemical instability to the system. That is, the chemical interaction between the printing inks and the polyurethane resin may cause premature gelling of the resin or a color change in the ink. As used herein, the term "gelling" has the same meaning as that used in U.S. Pat. No. 4,433,680.

Many printing substances cause a significant loss in the conformability of glass fiber casts. The printing is such that the conformability of the fiberglass substrate should not be compromised significantly after printing inks are dried and cured. This is the obvious need for the conformability of the substrate in order to provide good fracture immobilization.

Because the glass fiber surface would not readily absorb the pigments, large quantities of inks must be applied in order for the inks to become locked in the interstices of the fabric. However, in the case where the cured inks become hard, the interstices of the substrate become locked which causes a loss in stretchability and conformability of the fabric. It is therefore desirable to have systems which remain flexible after curing and permit the application of thin layers of prints to the surface so that there is little effect on the conformability of the casting tape.

SUMMARY OF THE INVENTION

It has, therefore, been found that suitable orthopaedic casting bandages made from fibers having a Young's Modulus greater than $8 \times 10^6$ pounds per square inch such as glass fibers and carbon fibers may be made using plastisol-based or water-based acrylic inks. The bandages comprised of a fibrous substrate having a surface at least 50% of the fibers of which have a Young's Modulus greater than $8 \times 10^6$ psi. In the case of plastisol ink, a printing material is placed on the surface and is comprised of a plastisol and pigment and other additives. A curable resin is then coated on the substrate over the printing material in order to provide the curable bandage characteristics.

In particular, the plastisol may be a formulation of polyvinyl chloride and a plasticizer or plasticizers. The preferred plastisols are monomeric ester type consisting mainly of the cyclic esters based on aromatic structure of benzene as represented by phthalates, trimelltates and others. The most preferred plasticizer is dioctylterephthalate.

Alternatively, it has been found that a water-based acrylic printing ink may be used to print the fiberglass. In this case, the water-based acrylic, which may be an emulsion of the acrylic polymer in water, is used as the base vehicle for the printing and pigments are added thereto in various quantities in order to obtain the desired colors.

Either of the two printing inks may be applied on substrates using a belt screen printer and then cured.

DETAILED DESCRIPTION OF THE INVENTION

Figure 1:
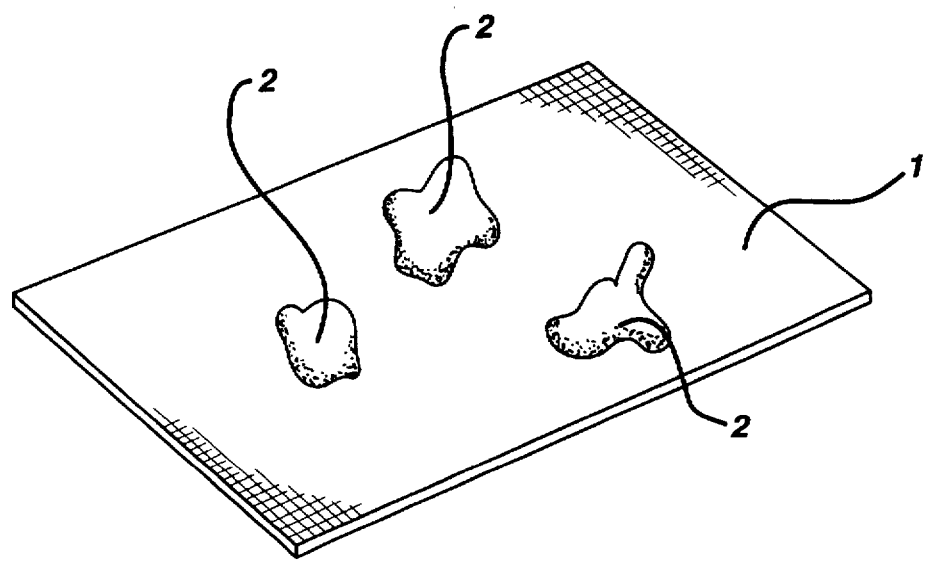
FIG. 1 is a perspective view of the orthopaedic casting bandage of the invention.
Figure 2:
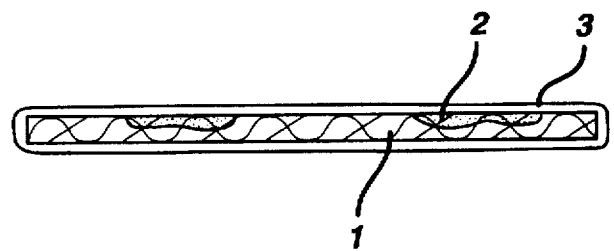
FIG. 2 is a cross-section of FIG. 1.

The invention will be described with reference to Figures showing substrates made of glass fibers. However, the invention is equally applicable to substrates made from fibers having a Young's Modulus which is greater than $8 \times 10^6$ psi such as fiberglass or carbon fibers. Normally, more than 50 percent of the printing surface should be covered with these fibers.

The fiberglass substrate 1 is a Rashel knitted fabric made according to known knitted substrate methods, the substrate is 100% glass fibers and printed on the surface of the fiberglass substrate is a pattern 2 which is formed of a plastisol based ink. The plastisol ink is typically made of a formulation of plastisol and pigment. The pigments are present in sufficient quantity to obtain the desired color and the plastisol is a vehicle to keep pigments on the substrate. The plastisol is a dispersion of polyvinyl latex particles in a plasticizer. A typical composition is 100 parts resin to about 100 parts plasticizer which forms a paste that fuses when heated.

The bandage is then coated with a polyurethane prepolymer which is comprised of polyols, isocyanate, catalyst and other additives. Such prepolymers are described in the Yoon patent '680 mentioned above.

A fiberglass substrate was formed from 100 percent fiberglass yarns knitted in a known fashion to form a substrate having a width of three inches. The substrate was printed with a plastisol-based ink using a silk screening print method. The ink colors were green, pink, blue and black.

The ink was applied using a standard screen printing process having a screen mesh number between 100 and 400. Four successive printing operations were performed in order to formulate the four-colored pattern used. After printing, the substrate was placed on a conveyer belt and passed through a curing oven. The curing was performed at 325° F. for ninety seconds. After curing, the inks were dry and cured. No discoloration to the inks was noted, and the fiberglass substrate appeared to not be significantly affected. There was minor dimensional shrinkage in the substrate due to the heat, however, the shrinkage was considered insignificant. The cured inks were soft and permitted flexing of the substrate.

After printing, the substrate was coated with a water-curable polyurethane resin made in accordance with Example 1 of the '680 patent. Bandages four yards in length were packaged in water impervious aluminum pouches and sealed. The pouches, with their contents, were aged for 14 days at 70° C. When the bandage was open, the inks did not show signs of bleeding, and the printing pattern had not degraded after the shelf life test. The four printing substances were formed with the following formulations. The black consisted of 90% by weight plastisol and 10% by weight pigment, the pigment is itself 80% by weight DINP and 20% carbon black.

The magenta was formulated from 95% by weight plastisol and 5% by weight pigment. The pigment was itself made from 50% by weight DINP and 50% fluorescent pigment.

The blue was made from 95% by weight plastisol and 5% by weight pigment; the pigment itself was made from 45% by weight DINP and 55% by weight fluorescent blue dyed polymer.

The green was made from 95% by weight plastisol and 2.5% by weight each of a yellow and green pigment. The pigments themselves were made from 67% by weight DINP and 33% by weight of a yellow pigment and green pigment.

EXAMPLE I

In the present Example, a satellite carousel printer was used and was equipped with a monofilament polyester screen having a mesh size of 286. The screen tension was 24 neutons. During the printing operation, various squeegee pressures were used in order to eliminate ink soak through in a known manner. During the curing process, the fabric web was passed through a thermal conveyer, and the heating ranges were between 300° F. and 320° F. Curing time lasted between 1.5 and 3 minutes.

EXAMPLE II

The bandages were made from the printed substrate in Example I by coating a water curable polyurethane prepolymer as in the '680 Yoon patent. After the bandages were sealed in aluminum foil pouches and aged for 14 days at 70° C., the bandages were open for evaluation. The printed patterns were not degraded.

EXAMPLE III

A roll of three-inch wide knitted fiberglass substrate was placed on a shaft over the edge of 13 yard-long multicolor belt printer. As the substrate unrolls, the rear of the tape is secured on the belt with glue, and the substrate moves with the belt at the speed of 14 yards per minute. Art work was engraved on four 38"×74" screens with 280 mesh and made of polyester monofilament. Four screens with 5 magnetized bar and four different water-based acrylic printing inks were secured over the belt. As the substrate travels with belt, four screens with black, green, blue and red printing inks are lowered at different time to print the prefabricated designs on the screens onto the fiberglass. The printed fiberglass is then lifted at the end of the belt and fed into the curing oven maintained at 275°–300° F. Total curing time is between 2.5 to 3 minutes.

EXAMPLE IV

A roll of four-inch wide knitted fiberglass tape was placed on the shaft as Example I. Designs were engraved on polyester monofilament screens with 220 mesh. Green, blue and red color acrylic inks were printed on the fiberglass using 8 magnetized bar and black color was printed using 6 magnetized bar. The curing condition was the same as Example I.

EXAMPLE V

To insure strong adhesion of water-based acrylic printing inks on the surface of fiberglass filament, to maintain no run down of the printing inks on the fiberglass surface and to maintain good cast appearance, a combination of 6 and 4 magnetized bars were used for the fiberglass printing.

EXAMPLE VI

The bandages were made from the substrates in Examples III, IV and V by coating a water-curable polyurethane prepolymer as in the '680 Yoon patent. After the bandages sealed in aluminum foil pouches and were aged for 14 days at 70° C., the bandages were open for evaluation. The printed patterns were not degraded at all in all the samples. The crush strengths data did not show any significant changes in comparison with a non-printed control sample.

What is claimed is:

1. An orthopaedic bandage comprising:

a. a fibrous substrate having a surface at least 50% of the fibers on said surface having a Young's Modulus greater than $8 \times 10^6$ pounds per square inch;

b. printing material on said surface comprised of a plastisol and pigment; and c. a curable resin coating on said substrate and said printing material.

2. The bandage according to claim 1 wherein said plastisol is a formulation of polyvinyl latex and plasticizer.

3. The bandage according to claim 2 wherein the plasticizer is dioctylterephthalate.

4. The bandage according to claim 1 wherein the curable resin is a water-curable resin.

5. The bandage according to claim 4 wherein the curable resin is an isocyanate terminated polyurethane prepolymer.

6. An orthopaedic bandage comprising:

a. a fibrous substrate having a surface at least 50% of the fibers on said surface having a Young's Modulus greater than $8 \times 10^6$ pounds per square inch;

b. a printing material on said surface comprised of a water-based acrylic and pigment; and c. a curable resin coating on said substrate and said printing material.

7. The orthopaedic bandage according to claim 6 further comprising a polyurethane stabilizer for stabilizing the pigments.

8. The orthopaedic bandage according to claim 6 wherein the water-based acrylic resin is an emulsion and the printing material comprises from 90% to 98% acrylic water emulsion and from 2% to 10% pigment.

* * * * *